US008481801B2

(12) United States Patent
Addison et al.

(10) Patent No.: US 8,481,801 B2
(45) Date of Patent: Jul. 9, 2013

(54) FLUID WOUND DRESSING COMPRISING PARTIALLY CURED POLYURETHANE

(75) Inventors: Deborah Addison, Keasden (GB);
Edward Schonfeld, Princeton, NJ (US);
Peter Wachtel, Scotch Plains, NJ (US);
Sally-Anne Stephens, Skipton (GB)

(73) Assignee: Systagenix Wound Management (US), Inc (GB)

( * ) Notice: Subject to any disclaimer, the term of this patent is extended or adjusted under 35 U.S.C. 154(b) by 422 days.

(21) Appl. No.: 12/470,620

(22) Filed: May 22, 2009

(65) Prior Publication Data

US 2009/0275872 A1 Nov. 5, 2009

Related U.S. Application Data

(62) Division of application No. 10/532,520, filed as application No. PCT/GB03/04609 on Oct. 24, 2003, now Pat. No. 7,538,257.

(60) Provisional application No. 60/421,085, filed on Oct. 25, 2002.

(30) Foreign Application Priority Data

Feb. 19, 2003 (GB) .................................. 0303821.3

(51) Int. Cl.
*A61F 13/00* (2006.01)
(52) U.S. Cl.
USPC .................... 602/48; 602/42; 602/43; 602/46
(58) Field of Classification Search
USPC ............................................. 602/41–59, 6–8
See application file for complete search history.

(56) References Cited

U.S. PATENT DOCUMENTS

| 4,170,697 | A | * | 10/1979 | Blount ............................ 521/82 |
| 4,542,012 | A | | 9/1985 | Dell |
| 4,551,518 | A | | 11/1985 | Matsumoto et al. |
| 4,614,787 | A | | 9/1986 | Szycher et al. |
| 4,969,880 | A | | 11/1990 | Zamierowski |
| 5,135,964 | A | | 8/1992 | Lee et al. |
| 5,192,536 | A | | 3/1993 | Huprich |
| 5,699,902 | A | * | 12/1997 | Sperry et al. .................. 206/219 |
| 5,844,013 | A | | 12/1998 | Kenndoff et al. |
| 6,054,504 | A | * | 4/2000 | Dalla Riva Toma .......... 523/122 |
| 6,303,731 | B1 | | 10/2001 | Carlson et al. |

FOREIGN PATENT DOCUMENTS

| EP | 0 269 071 | | 6/1988 |
| EP | 0 336 406 | | 10/1989 |
| SU | 407927 A | * | 4/1974 |
| WO | WO 9952569 A1 | * | 10/1999 |
| WO | 2007/115781 | | 10/2007 |
| WO | 2009/043499 | | 4/2009 |

* cited by examiner

*Primary Examiner* — Kim M Lewis
(74) *Attorney, Agent, or Firm* — Brian B. Shaw, Esq.; Paul A. Leipold, Esq.; Harter Secrest & Emery LLP

(57) ABSTRACT

A wound dressing composition comprising a partially cured polyurethane fluid. The composition can be injected directly into a wound, where it cures to form a wound filling dressing. Also provided is a wound dressing comprising such a composition. Also provided is a kit for the preparation of such wound dressings, the kit comprising (a) a polyurethane prepolymer; and (b) a curing agent for the polyurethane prepolymer. Preferably, the polyurethane components comprise reaction products of a diisocyanate with castor oil or a related ester of ricinoleic acid or its derivatives.

9 Claims, No Drawings

FLUID WOUND DRESSING COMPRISING PARTIALLY CURED POLYURETHANE

STATEMENT OF RELATED APPLICATIONS

This application is a divisional of, and claims the benefit of, U.S. patent application Ser. No. 10/532,520, filed Jan. 30, 2006, currently pending, which is a U.S. National Stage of International Application No. PCT/GB2003/004609, filed Oct. 24, 2003, which in turn claims the benefit of Great Britain Application No. 0303821.3, filed Feb. 19, 2003, and U.S. Provisional Application No. 60/421,085, filed Oct. 25, 2002, each of which is incorporated herein by reference, in its entirety.

The present invention relates to fluid wound dressings that can be used to fill cavity wounds.

Cavity wounds can be a problem to treat due to high levels of exudate production, the irregular contours of the wound site, the loss of tissue (sometimes undermining the surrounding skin) and the potential for tracts or sinuses. The full extent of the cavity wound is not always obvious, from a visual assessment, which complicates the treatment choice.

The main wound management regime for cavity wounds is much the same as for other wounds, that is to say moist wound healing and exudate management. The standard treatments tend to be based around packing the cavity with gauze, alginates or some other absorbent material. This primary dressing is often held in place with a secondary dressing, such as a film, foam or gauze, depending on the level of exudation.

The extent to which a cavity wound is packed is determined by the caregiver and should be dependent on the packing material. There is a tendency to over-pack cavity wounds, which may result on detrimental pressure being applied to the wound bed.

The care giver also needs to ensure that all of the cavity wound dressing is removed after treatment, unless the dressing is fully bioresorbable.

Cavity wounds can be heavily exuding, and it is therefore desirable to use a cavity wound filling material that can transport material by capillary action or diffusion from the wound site to a moisture-absorbent secondary dressing.

It is known to provide textile or foam-based absorbent structures for dressing deep wounds. Those structures are insufficiently conformable to fit every deep wound, unless they are cut into shape. Furthermore, such absorbent structures can be relatively difficult to remove from a deep wound after use without causing further trauma.

U.S. Pat. No. 4,837,285 describes the use for soft tissue cavity filling of resorbable collagen sponge beads having diameters of from 0.1 to 4.0 mm. The beads have pore sizes of from 50 to 350 micrometers. Such beads can be difficult to handle, and are not suitable for use as a removable, absorbent dressing for deep wounds.

DE-A-4037931 describes a deep cavity wound dressing structure consisting of a cavity-filling plug of resorbable collagen foam containing an array of hollow resorbable filaments. The filaments are bundled together at one end, and connected to a drain for wound fluid, whereby the wound fluid is continuously drained from the wound cavity through the hollow filaments. Such a structure is relatively expensive to construct, and insufficiently conformable to a wide range of wound cavity shapes.

EP-A-0171268 describes absorbent, non-adherent wound dressings for use in the treatment of deep wounds, wherein the dressing comprises a porous bag containing individual pieces of a conformable, resilient, absorbent hydrophilic, foam. The porous bag may be provided with a string to assist removal of the bag from the wound after use. This structure may be insufficiently conformable to a wide range of wound cavity shapes.

The present invention provides a wound dressing composition comprising a partially cured polyurethane fluid.

The term "wound dressing composition" refers to a composition suitable for injection directly into wounds to provide a dressing for the wound. It does not encompass hardening compositions for orthopedic casts or the like. The term "polyurethane" in this specification encompasses polymers comprising urethane and/or urea-linkages.

The wound dressing according to the present invention is a fluid. The fluid may be a liquid, preferably a viscous liquid, or it may be a paste, or it may be a non-Newtonian fluid. This property makes the wound dressing composition especially suitable for completely filling a cavity wound by injection or pouring, or simply by working the fluid into the wound cavity in with a spatula or similar implement.

The wound dressing composition comprises a partially cured polyurethane fluid. Preferably, it comprises at least 50% by weight of the polyurethane components, and more preferably at least 75%, 90%, or 95% by weight of the polyurethane components. The polyurethane fluid is partially cured. That is to say, it has been prepared by mixing a diisocyanate or a polyisocyanate composition with a curing composition, such as a diol or polyol composition, but the reaction between the components has not gone to completion. For example, at least 1% of the isocyanate groups originally present in the isocyanate composition may still be present (i.e. unreacted) in the wound dressing, preferably at least 10% thereof may still be present, and typically from 20% to 75% are still present. However, it should be noted that preferably the absolute amount of unreacted isocyanate in the wound dressing composition is low, in order to reduce adverse reaction of isocyanate in vivo. Preferably, the absolute amount of unreacted isocyanate present in the composition according to the invention is less than about 4 wt. % (i.e. about 1 meq NCO/gram), more preferably less than about 2 wt. %, and most preferably from about 0.1 wt. % to about 1 wt. %.

Suitable components for the preparation of wound dressing compositions according to the present invention are described below in connection with the third aspect of the present invention.

The polyurethane fluid starts to cure on mixing of the two components and continues to cure in situ in the wound to form a wound filling dressing that conforms exactly to the shape of the wound. The resulting cured polyurethane is preferably soft and flexible for comfort, but preferably has sufficient wet and dry tensile strength to be removed in one piece from the wound after use. Preferably, the dry tensile strength of the as-cured polyurethane is at least about $5N/cm^2$, more preferably at least about $10N/cm^2$. Preferably, the wet tensile strength after immersion in physiological saline for 24 hours at 25° C. is at least 50% of the dry tensile strength, more preferably at least 75% of the dry tensile strength.

The cured polyurethane is preferably sufficiently hydrophilic to wick exudate from the wound to a secondary dressing, but preferably does not absorb enough wound fluid to give rise to swelling that would exert undesirable pressure. Preferably, the absorbency of physiological saline at 25° C. after 24 hours is less than 200 wt. % based on the weight of the as-cured polyurethane, more preferably less than 100 wt. %.

In certain embodiments the wound dressing composition comprises additives, for example selected from the group consisting of humectants, plasticisers, hydrocolloids, blowing agents, medicaments, siloxane wetting agents and mixtures thereof.

The optional plasticisers assist in providing a flexible, soft cured polyurethane in situ in the wound. Suitable plasticisers include medically acceptable mineral oils, silicone oils, vegetable oils, stearates, hydrogenated ethers and esters, and mixtures thereof.

The optional humectants assist in maintaining the desired moist wound healing environment in situ in the wound. Suitable humectants include medically acceptable polyhydric alcohols such as glycerol, sorbitol, soft paraffin, urea creams, lanoline, sodium pyrrolidone carboxylate (PCANa), gamma linolenic acid (evening primrose oil) and soya oil, tea tree oil, coconut oil (or any other nut oil), camomile, aloe vera, jojoba oil, cocoamide or mixtures thereof.

The optional hydrocolloids assist in adjusting the water absorbency and wicking properties of the cured polyurethane composition. Suitable hydrocolloids include alginates, pectin, gums such as guar gum or xanthan gum, modified celluloses such as carboxymethyl cellulose and hydroxyethyl cellulose, modified starches such as sodium starch glycolate, and mixtures thereof.

The optional blowing agents provide the cured polyurethane with a foamed or porous structure to increase its permeability to wound fluid. Suitable blowing agents include water (which reacts with isocyanate groups to form urea linkages and carbon dioxide), and citric acid/sodium bicarbonate or formic acid or hydrofluorocarbon.

Preferably, the wound dressing compositions according to the invention have a curing time of from about 0.1 to about 180 minutes, preferably about 2 to about 30 minutes.

The optional siloxane wetting agents provide the cured polyurethane with increased wetting or wicking properties. Suitable surfactants include dimethyl siloxanes, PLURONICS (Registered Trade Mark of BASF), BRIJ (Registered Trade Mark of ICI) or mixtures thereof.

In a second aspect, the present invention provides a wound dressing comprising a wound dressing composition according to the first aspect of the invention.

The wound dressing according to this aspect of the invention may further comprise reinforcing elements to assist removal of the cured polyurethane composition it one piece from the wound. Suitable reinforcing elements include woven or nonwoven fabrics, polymer webs or meshes. The reinforcing elements may be introduced into the wound cavity before, during or immediately after introduction of the partially cured polyurethane fluid.

The wound dressing according to the invention may further comprise drainage elements to assist drainage of exudate from wounds. Suitable drainage elements includes flexible polymeric tubes and flexible biodegradable tubes, such as those described in DE-A-4037931, the entire content of which is incorporated herein by reference.

In a third aspect, the present invention provides a wound dressing kit comprising: (a) a polyurethane prepolymer; and (b) a curing agent for the polyurethane prepolymer.

The components (a) and (b) are adapted to be used in combination to form a wound dressing composition according to the present invention. In certain embodiments, the components (a) and (b) are stored separately in a single package for mixing immediately before use. The package may comprise a barrier between the components that can be opened to allow the components to mix inside the package immediately before use. In other embodiments, the package may comprise a mixing chamber for sterile mixing of the components immediately before use.

The wound dressing kit is adapted for the preparation of a wound dressing according to the invention by mixing of components (a) and (b). The kit may further comprise reinforcing elements and/or drainage elements as hereinbefore described. It may further comprise a secondary dressing for application over the wound dressing of the invention.

Preferably, both component (a) and component (b) are liquid at temperatures above 10° C., preferably at temperatures above 5° C., and more preferably at temperatures above 0° C. This assists mixing of the components at ambient temperatures.

Component (a)

Component (a) preferably comprises an isocyanate capped prepolymer.

Preferably, the isocyanate-capped prepolymer comprises from 0.1 to 1 meq NCO groups/g. In certain embodiments the isocyanate-capped prepolymer is an isocyanate-capped polyether or polyester prepolymer. For example, the prepolymer may be an isocyanate-capped oxyethylene/oxypropylene copolymer. This enables the properties of the polyurethane to be regulated by varying the ration of ethylene oxide to propylene oxide in the prepolymer (high ethylene oxide gives a more hydrophilic product).

In certain embodiments, component (a) may be an isocyanate-capped castor oil, or derivative thereof. For example, component (a) may be produced by reacting a diisocyanate such as isophorone diisocyanate (IPDI) with castor oil, or a glycerol mono- or diester of ricinoleic acid, or a derivative thereof produced by reaction with ethylene oxide or propylene oxide such as CASPOL 5001 or other ricinoleic acid derivatives such as CASPOL 5003.

Preferably, the prepolymer is a reaction product of an aliphatic isocyanate, since polyurethanes manufactured from aliphatic isocyanates have superior mechanical properties and superior light stability. The isocyanates used in the prepolymer reaction can be selected from, but not limited to the following:

1,4 tetramethylene diisocyanate
1,6 hexamethyl dilsocyanate (Bayer's Desmodur H)
Isophorone diisocyanate (IPDI)
Methylene bis(4-cyclohexyl)-isocyanate
Meta or para xylylene diisocyanate
Degussa's T-6040 (a mixture of IPDI and its trimer)
Isomeric mixtures of any of the above.

Commercially available isocyanate capped prepolymers include Degussa's Vestanat (Registered Trade Mark) EPU-937 prepolymer based on IPDI. Other prepolymers could include the HYPOLs (although not aliphatic, they would still work) and other aliphatic prepolymers based on $H_{12}MDI$ (4,4'-dicyclohexylmethane diisocyanate) or CHDI (Trans 1,4-cyclohexane diisocyanate)

Component (a) may further comprise the plasticisers, humectants and hydrocolloids.

Component (b)

A preferred polyol for preparation of the wound dressings and wound dressing kits according to the present invention is castor oil and other esters of ricinoleic acid and its derivatives. One such derivative is a monoricinoleate ester to which either ethylene oxide or propylene oxide has been added to the hydroxyl group on the ricinoleate, available under the Registered Trade Mark CASPOL 5001.

It has been found that the branched structure of the castor oil and derivatives thereof breaks up the symmetrical orientation of the polyurethane molecules, and allows the prepolymer to remain fluid at temperatures as low as 4° C. This provides further advantages in the preparation of fluid wound dressing compositions at ambient temperatures.

In certain embodiments, component (b) comprises water as a foaming and polymerising agent. The water in the component (b) reacts with the isocyanate prepolymer to cross-link the isocyanate groups in urea linkages and release $CO_2$, which causes the polyurethane reaction mixture to form a foam. Preferably, the amount of water in the component (b) is from 0.02 to 0.1 parts by weight per part by weight of the isocyanate prepolymer.

In certain embodiments, component (b) comprises chain extending or terminating agents, catalysts or mixtures thereof. For example, component (b) may comprise diamine chain extending/terminating compounds such as 1,4-butane diol, 1,5-pentane diol or 1,6-hexane diol or diamines such as DDM (4,4'-diaminodiphenylmethane) or DAB (1,3-diaminobenzene).

In certain embodiments, component (b) further comprises a catalyst for the polymerisation, preferably a diamine such as diazobicyclo octane or dimethylaminoethyl ether. Preferably, the catalysts are present in component (b) in an amount of 0:005 to 0:02 parts by weight, based on one part by weight of the isocyanate prepolymer. Catalysts such as tertiary amines and organometal compounds, most preferably organotin catalysts may also be present. The catalyst to be employed should be a non-cytotoxic catalyst, for example one of the catalysts listed in U.S. Pat. No. 4,332,927, the entire content of which is incorporated herein by reference. For example, an organotin derivative made with castor oil.

In certain embodiments, the component (b) comprises a polyurethane or polyurea chain terminating compound, preferably selected from monohydric alcohols and amines. More preferably, the component (b) comprises a mixture of monoamines and diamines. The amounts of chain extending and terminating compounds influence the physical properties of the foam. In particular, amine/diamine chain terminating/extending compounds react with the prepolymer very much faster than water and alcohols. For example, the tackiness of the foam increases with increasing monohydric alcohol or monoamine content in component (b). Preferably, the chain extending and terminating compounds are present in component (b) in an amount of 0.05 to 0.4 parts for alcohols and 0.01 to 0.05 parts for the amines, based on one part by weight of the isocyanate prepolymer.

The blowing agents and surfactants may also be present in component (b).

Component (b) may comprise wound therapeutic materials. Suitable therapeutic materials include: antiseptics such as molecular silver, silver sulfadiazine or chlorhexidine; pain relieving agents such as lignocaine; anti-scarring agents such as mannose-6-phosphate, and agents for promoting wound healing such as growth factors.

In a further aspect, the present invention provides the use of components (a) and (b) as hereinbefore described for the preparation of a wound dressing composition comprising a partially cured polyurethane fluid for application directly to a wound as a wound dressing. Preferably, the wound dressing composition is a composition according to the first aspect of the present invention.

The present invention further provides a method of treatment of a wound comprising applying thereto a wound dressing composition comprising a partially cured polyurethane fluid. Preferably, the wound dressing composition is a composition according to the first aspect of the present invention. Preferably, the composition is applied so as to substantially completely fill the wound. The composition is allowed to cure in the wound.

It will be appreciated that any features that are described as optional or preferred in connection with any one aspect of the present invention are likewise optional or preferred in connection with any other aspect of the invention. Thus, for example, the components (a) and (b) described in connection with the kits according to the present invention may be mixed to prepare a wound dressing composition according to any embodiment of the first aspect of the invention.

Specific embodiments of the present invention will now be described further, by way of example. In the examples, the following abbreviations and trade names are used:

VESTANAT (Degussa) A prepolymer based on isophorone diisocyanate.

T-6040 (Degussa) A mixture of isophorone diisocyanate and its trimer

EPU-937 (Degussa) A prepolymer based on isophorone diisocyanate.

CASPOL 5001 (CasChem) A dihydroxy castor oil derivative

ACCLAIM (Bayer) A polypropylene glycol

VORANOL (Dow) A polyol

COTIN (CasChem) A proprietary urethane catalyst

POLY G 55-53 (Arch) A PEO/PPO polyol containing 27% ethylene oxide.

AVICEL

AC-DI-SOL

Purity Gum 59 A low viscosity starch derived from waxy maize

SAFOAM B A sodium hydrogen carbonate or sodium bicarbonate

EXAMPLE 1

In order to reduce the initial concentration of available NCO in the wound dressing below 3.8%, a prepolymer was prepared as follows.

The prepolymer was prepared by reacting a mixture of Glycerol based polyether potyol (Poly-G-76-120) and a hydroxy terminated polyoxyalkylene polyol (Poly-G-55-56) with VERSANAT IPDI and sufficient catalyst (Cotin1707) to form the desired prepolymer.

The prepolymer had an NCO content of less than 5% resulting in a lower initial NCO value of the final wound dressing.

A wound dressing was made using the prepolymer prepared above in component (a). A dressing was prepared using two different methods: (1) mixing the components and pouring the mixture into a plastic cup and (2) mixing the components and coating the mixture onto a release liner. After curing, the coated film was stripped from the release liner and die cut into ribbon and various other shapes. An attractive, sponge-like product was obtained. The strips exhibited very good mechanical integrity both wet and dry.

The components of the representative product are as follows:

| | |
|---|---|
| Caspol 5003 | 23% |
| Castor Oil | 6 |
| Poly G 55-56 | 10.5 |
| T-6040 | 16 |
| EPU-937 | 15 |
| Soybean Oil | 4 |
| Purity Gum 59 | 4 |
| Avicel | 17 |
| Ac-di-Sol | <1 |
| Cotin 1707 | <1 |
| Citric Acid | <1 |
| NaCarbonate | <1 |
| Safoam B | <1 |

This composition can be adjusted to obtain a softer wound dressing. The composition of the above formulation is used here as an example to demonstrate the isocyanate concentration of an initial prototype composition as a function of time.

The measured free NCO of the prepolymer before final compounding was less than 5%. It should be kept in mind that the formulation is catalysed, and when the catalysed and un-catalysed portions are mixed together, reaction quickly occurs. Accordingly, available NCO was determined by titration immediately after mixing, and also after 15 and 30 minutes. The data is presented in the following table:

| TIME (MINUTES) | % NCO |
| --- | --- |
| Theoretical | Less than 5.0 |
| Actual Initial | 2.7 |
| 15 | 0.6 |
| 30 | <0.1 |

Replacement of the glycol present in EPU-937 with a larger molecular weight glycol reduces the NCO content even further.

Tensile strengths are quite remarkable. Initial data generated on drawn down samples prepared from the polymer in the previously described example indicate that tensile was greater than 2,000 grams per inch width sample. After water immersion for 24 hours, the loss of tensile strength is less than 10%.

The above example has been described by way of illustration only. Many other embodiments falling within the scope of the accompanying claims will be apparent to the skilled reader.

The invention claimed is:

1. A wound dressing kit, comprising:
   (a) a polyurethane prepolymer, comprising an isocyanate capped prepolymer and a compound selected from the group consisting of castor oil, other esters of ricinoleic acid, and derivatives thereof, wherein the polyurethane prepolymer is prepared by reacting a disocyanate with the compound selected from the group consisting of castor oil, glycerol mono- or diester of ricinoleic acid and other ricinoleic acid derivatives thereof; and
   (b) a curing agent for the polyurethane prepolymer;
   wherein components (a) and (b) are stored separately in a single package for mixing immediately before use to form a combined preparation; and
   wherein a portion of the isocyanate capped prepolymer remains uncured resulting in a soft and flexible polyurethane having a dry tensile strength of at least $5N/cm^2$.

2. The wound dressing kit according to claim 1, wherein the package comprises a barrier between the components that can be opened to allow the components to mix inside the package immediately before use.

3. The wound dressing kit according to claim 1, wherein the package comprises a mixing chamber for sterile mixing of the components immediately before use.

4. The wound dressing kit of claim 3 further comprising a secondary dressing.

5. The wound dressing kit of claim 4 wherein the combined preparation is suitable for application directly from the mixing chamber onto a wound.

6. The wound dressing kit according to claim 1, further comprising one or more of the group consisting of reinforcing elements, drainage elements, and a secondary dressing.

7. The wound dressing kit according to claim 1, wherein component (a) and component (b) are both liquids at temperatures above 5° C.

8. The wound dressing kit according to claim 1, wherein component (b) comprises a wound therapeutic material selected from the group consisting of antiseptics such as molecular silver, silver sulfadiazine or chlorhexidine; pain relieving agents such as lignocaine; anti-scarring agents such as mannose-6-phosphate, and agents for promoting wound healing such as growth factors, and mixtures thereof.

9. The wound dressing kit of claim 1 wherein component (b) further comprises a blowing agent.

* * * * *